United States Patent [19]

Gaughan

[11] 4,250,185  
[45] Feb. 10, 1981

[54] 1-(3,5-DICHLOROBENZOYL)-3-PHENYL-PYRAZOLINES AND THEIR USE AS MILDEWICIDES

[75] Inventor: Edmund J. Gaughan, Berkeley, Calif.

[73] Assignee: Stauffer Chemical Company, Westport, Conn.

[21] Appl. No.: 128,687

[22] Filed: Mar. 10, 1980

[51] Int. Cl.³ .................... A01N 43/56; C07D 231/06
[52] U.S. Cl. .................... 424/273 P; 548/379
[58] Field of Search ............... 548/379, 378; 424/273 P

[56] References Cited

U.S. PATENT DOCUMENTS 4,140,787  2/1979  Sirrenberg et al. ............... 548/379

OTHER PUBLICATIONS

Freudenberg et al., Annalen 1924, vol. 440, pp. 38–45.

Primary Examiner—Henry R. Jiles  
Assistant Examiner—Natalia Harkaway  
Attorney, Agent, or Firm—Edwin H. Baker

[57] ABSTRACT

Certain 1-(3,5-dichlorobenzoyl)-3-phenylpyrazolines which have the structural formula

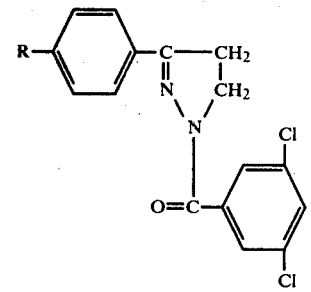

where R is hydrogen, alkyl, alkoxy or halo and their uses as a mildewicide.

8 Claims, No Drawings

1-(3,5-DICHLOROBENZOYL)-3-PHENYLPYRAZO-LINES AND THEIR USE AS MILDEWICIDES

BACKGROUND OF THE INVENTION

This invention relates to certain 1-(3,5-dichlorobenzoyl)-3-phenylpyrazolines which are useful as a mildewicide.

DESCRIPTION OF THE INVENTION

The compounds of the present invention are certain 1-(3,5-dichlorobenzoyl)-3-phenylpyrazolines and have the following structural formula

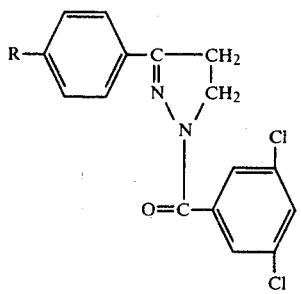

where R is hydrogen, alkyl having 1 to 4 carbon atoms, preferably methyl, alkoxy having 1 to 4 carbon atoms, preferably methoxy or halo, preferably chloro.

In the above description of the compounds of this invention, alkyl includes both straight chain and branched chain configurations, for example, methyl, ethyl, n-propyl, isopropyl, n-butyl, sec-butyl or tert. butyl. The term halo includes chlorine, bromine, iodine and fluorine.

The compounds of the present invention can be prepared by the following general method.

Reaction No. 1

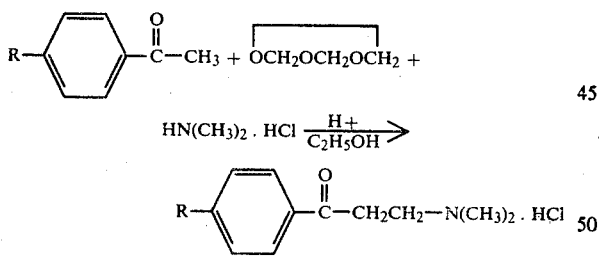

wherein R is as previously defined.

Generally, a mole amount of the acetophenone reactant and a slight excess of both dimethylamine hydrochloride and paraformaldehyde dissolved in a solvent such as ethanol are heated to reflux with stirring. Next, the reaction mixture is refluxed for about 4 hours with a catalytic amount of hydrochloric acid. Thereafter, the mixture is cooled and acetone is added to precipitate the desired reaction product.

Reaction No. 2

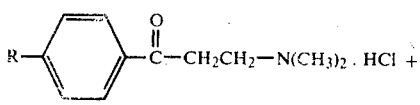

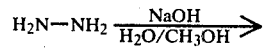

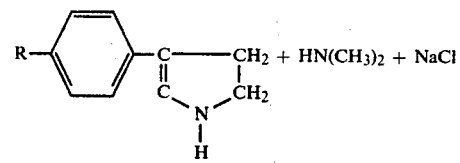

wherein R is as previously defined.

Generally, mole amounts of hydrazine hydrate and sodium hydroxide (as 50% solution in water) dissolved in methanol are heated to reflux with stirring. Next, a mole amount of the reaction product from Reaction No. 1 dissolved in a solvent such as methanol is added and the resulting mixture is refluxed for about 2 hours. Next, the solvent is removed under vacuum and methylene chloride solvent is added under an inert atmosphere to dissolve the reaction product. This solution is washed with $NaHCO_3$ solution and the organic phase dried under an inert atmosphere with $Na_2SO_4$ in the presence of a small amount of $Na_2CO_3$. The solution is filtered and the solvent stripped by vacuum to yield the desired solid reaction product. The product should be stored in the darkened area under an inert atmosphere in the cold.

Reaction No. 3

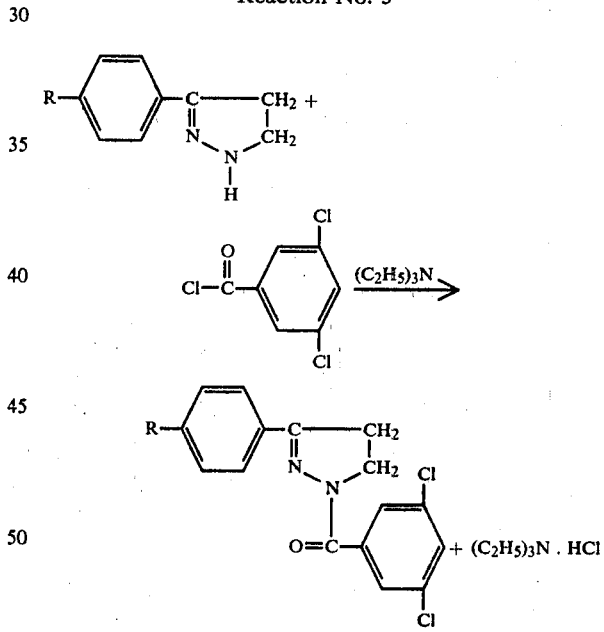

wherein R is as previously defined.

Generally, a mole amount of 3,5-dichlorobenzoylchloride dissolved in methylene chloride is added to a solution of a mole amount of the reaction product of Reaction No. 2 and a mole amount of triethylamine at a temperature of $-10°$ C. to $-5°$ C. The mixture is stirred at room temperature for 2 hours and for ½ hour at 40° C. The resulting mixture is cooled, washed three times with water, twice with a dilute $NaHCO_3$ solution and one time with a saturated NaCl brine solution followed by drying. The solvent is removed by vacuum to yield the desired product.

Preparation of the compounds of this invention is illustrated by the following examples.

EXAMPLE I

3-(Dimethylamino)-4'-methyl propiophenone hydrochloride

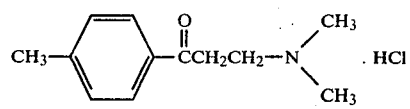

This example teaches a method of preparation for the reactant 3-(dimethylamino)-4'-methyl propiophenone hydrochloride.

53.6 Grams (g) (0.4 mole) of p-methylacetophenone, 42.4 g (0.52 mole) dimethylamine hydrochloride, 15.6 g (0.52 mole) paraformaldehyde and 64 milliliters (ml) ethanol were placed in a round-bottom flask equipped with a condenser and the mixture was heated to reflux with stirring. Next, 0.8 ml of concentrated hydrochloric acid was added to the mixture and refluxing was continued for 4 hours. The mixture was cooled and 600 ml of acetone was added. The desired product precipitated and was filtered and dried. m.p. 162°–163°. Yield: 70 g (76.9%).

EXAMPLE II

3-(4-Methylphenyl)-pyrazoline

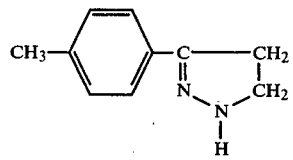

This example teaches a method of preparation for the reactant 3-(4-methylphenyl)-pyrazoline.

22.4 ml hydrazine hydrate, 50% sodium hydroxide solution (11.5 ml) and 28.8 ml methanol were placed in a round-bottom flask equipped with a stirrer and condenser and the mixture heated to reflux with stirring. Next, a solution of 24.8 g (0.16 mole) of 3-(dimethylamino)-4'-methyl propiophenone hydrochloride of Example I dissolved in 112 ml methanol was added to the above mixture and refluxing was continued for 2 hours with stirring.

The methanol was removed in vacuo. 200 ml methylene chloride was added to the residue under an argon atmosphere and this solution was washed rapidly with two 150 ml portions of a warm, saturated sodium bicarbonate solution. The organic phase was dried under an argon atmosphere with sodium sulfate in the presence of a small amount of sodium carbonate. The solution was kept in a darkened area and refrigerated during drying.

The solution was then filtered through Dicalite and the solvent removed in vacuo. The residue was pumped out under high vacuum to yield a light yellow solid which was stored in a refrigerator in a darkened area under an argon atmosphere. Yield: 16.1 g (62.5%).

EXAMPLE III

1-(3,5-Dichlorobenzoyl)-3-(4-methylphenyl)-pyrazoline

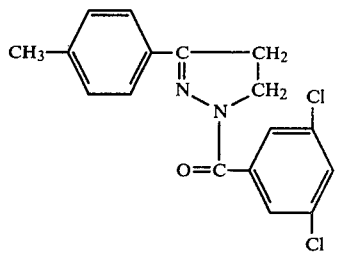

This example teaches a method of preparation for the compound 1-(3,5-dichlorobenzoyl)-3-(4-methylphenyl)-pyrazoline.

A solution of 6.3 g (0.03 mole) 3,5-dichlorobenzoyl chloride in 25 ml methylene chloride at −10° C. to −5° C. was added to a solution of 5.1 g (0.032 mole) pyrazoline, reactant of Example II, and 3.5 g (0.03 mole) triethylamine in 70 ml methylene chloride. The mixture was stirred for 2 hours at room temperature and ½ hour at 40° C. The resulting mixture was cooled, washed three times with water, twice with a dilute sodium bicarbonate solution, one time with saturated brine and dried. The solvent was removed in vacuo and the crude product was recrystallized from toluene to yield the desired product. m.p. 165°–168°. A yield of 3.5 g (35%) was realized and the structure was confirmed by infrared and mass spectroscopy.

The following is a table of certain selected compounds that are preparable according to the procedure described hereto. Compound numbers are assigned to each compound and are used throughout the remainder of the application.

TABLE I

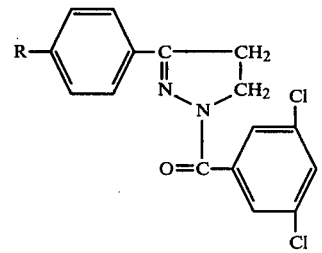

| Compound Number | R | Melting Point |
| --- | --- | --- |
| 1 | H | 120–132° C. |
| 2 | p-CH$_3$O | 129–130° C. |
| 3 | p-Cl | 190–191° C. |
| 4* | p-CH$_3$ | 165–168° C. |

*Prepared in Example III

FOLIAR MILDEWICIDE EVALUATION TESTS

A. Evaluation for Preventive Action

1. Bean Powdery Mildew Test

Pinto bean plants (*Phaseolus vulgaris* L.) approximately 10 cm tall are transplanted into sandy loam soil in three-inch clay pots. The plants are then inverted and dipped for two to three seconds in 50-50 acetone water solution of the test chemical. Test concentrations range from 1000 ppm downward. After the leaves are dried, they are dusted with spores of the bean powdery mildew (*Erysiphe polygoni* De Candolle) and held in the greenhouse until fungal growth appears on the leaf surface. Effectiveness is recorded as the lowest concentration, in ppm, which will provide 75% or greater reduction in mycelial formation as compared to untreated, inoculated plants. These values are recorded in Table II.

2. Barley Powdery Mildew Test

Barley leaves (*Hordeum vulgare*) are grown from seed in sandy loam soil to a height of approximately 10 cm in three-inch clay pots. The plants are then inverted and dipped for two to three seconds in 50-50 acetone water solution of the test chemical. Test concentrations range from 1000 ppm downward. After the leaves are dried, they are dusted with spores of the barley powdery mildew fungus (*Erysiphe graminis*) and held in the greenhouse until fungal growth appears on the leaf surface. Effectiveness is recorded as the lowest concentration, in ppm, which will provide 75% or greater reduction in mycelial formation as compared to untreated, inoculated plants. These values are recorded in Table II.

TABLE II

| Compound Number | Preventive Action | |
|---|---|---|
| | Bean Powdery Mildew | Barley Powdery Mildew |
| 1 | 1.0 | 10.0 |
| 2 | 5.0 | 10.0 |
| 3 | * | 500 |
| 4 | 1.0 | 5.0 |

*Not active at 1,000 ppm and not tested at a higher concentration

The compounds of this invention are generally embodied into a form suitable for convenient application. For example, the compounds can be embodied into a pesticidal composition which is provided in the form of emulsions, suspensions, solutions, dusts and aerosol sprays. In general, such compositions will contain, in addition to the active compound, the adjuvants which are found normally in pesticide preparations. In these compositions, an active compound of this invention can be employed as the sole pesticide component or it can be used in admixture with other compounds having similar utility. The pesticide compositions of this invention can contain, as adjuvants, organic solvents, such as sesame oil, xylene range solvents, heavy petroleum, etc.; water; emulsifying agents; surface active agents; talc; pyrophyllite; diatomite; gypsum; clays, propellants, such as dichlorodifluoromethane, etc. If desired, however, an active compound can be applied directly where control is desired.

The precise manner in which the pesticidal compositions of this invention are used in any particular instance will be readily apparent to a person skilled in the art. The concentration of the active compound in the present compositions can vary within rather wide limits, ordinarily the compound will comprise not more than about 15.0% by weight of the composition. Preferably, however, the pesticide compositions of this invention will be in the form of a solution or suspension containing up to about 1.0% by weight of the active pesticide compound.

I claim:
1. A compound having the formula

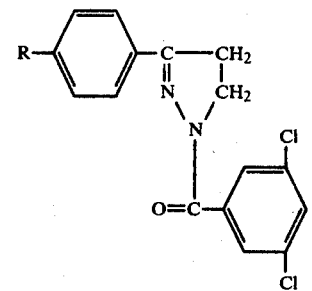

where R is hydrogen, alkyl having 1 to 4 carbon atoms, alkoxy having 1 to 4 carbon atoms or halo.

2. A compound of claim 1 wherein R is hydrogen, methyl, methoxy or chloro.
3. The compound of claim 1 wherein R is hydrogen.
4. The compound of claim 1 wherein R is methyl.
5. The compound of claim 1 wherein R is methoxy.
6. The compound of claim 1 wherein R is chloro.
7. A method of controlling mildew comprising applying thereto a moldewicidally effective amount of a compound having the formula

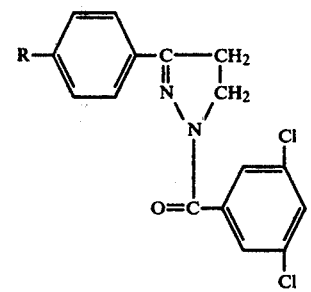

where R is hydrogen, alkyl having 1 to 4 carbon atoms, alkoxy having 1 to 4 carbon atoms or halo.

8. A mildewicidal composition comprising a mildewicidally effective amount of a compound having the formula

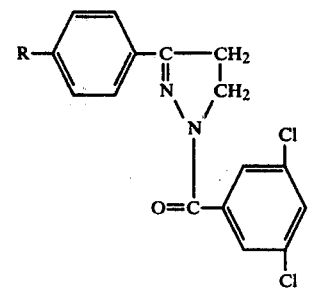

where R is hydrogen, alkyl having 1 to 4 carbon atoms, alkoxy having 1 to 4 carbon atoms or halo and an inert carrier.

* * * * *